US009956342B2

(12) United States Patent
Wurmbauer et al.

(10) Patent No.: US 9,956,342 B2
(45) Date of Patent: May 1, 2018

(54) INJECTION DEVICE

(71) Applicant: Ares Trading SA, Aubonne (CH)

(72) Inventors: Werner Wurmbauer, Maria Saal (AT); Josef Schopf, Aichdorf/Fohnsdorf (AT); Bernhard Schatz, Klagenfurt (AT)

(73) Assignee: ARES TRADING SA, Aubonne (CH)

( * ) Notice: Subject to any disclaimer, the term of this patent is extended or adjusted under 35 U.S.C. 154(b) by 447 days.

(21) Appl. No.: 14/407,979

(22) PCT Filed: Jun. 11, 2013

(86) PCT No.: PCT/IB2013/001212
§ 371 (c)(1),
(2) Date: Dec. 15, 2014

(87) PCT Pub. No.: WO2013/186617
PCT Pub. Date: Dec. 19, 2013

(65) Prior Publication Data
US 2015/0141923 A1    May 21, 2015

(30) Foreign Application Priority Data

Jun. 15, 2012  (EP) .................................... 12004542

(51) Int. Cl.
*A61M 5/20* (2006.01)
*A61M 5/32* (2006.01)
*A61M 5/24* (2006.01)
(52) U.S. Cl.
CPC ................ *A61M 5/20* (2013.01); *A61M 5/24* (2013.01); *A61M 5/3234* (2013.01);
(Continued)

(58) Field of Classification Search
CPC ................ A61M 5/3234; A61M 5/20; A61M 2005/2026; A61M 2005/208; A61M 2005/2073; A61M 2005/206
See application file for complete search history.

(56) References Cited

U.S. PATENT DOCUMENTS 3,630,417 A  *  12/1971  De Haas  .............  A61M 5/1452
                                                   222/333
2007/0197968 A1*  8/2007  Pongpairochana  .....  A61M 5/20
                                                   604/131

FOREIGN PATENT DOCUMENTS

JP           067444 A    1/1994
JP      2011520569 A    7/2011
(Continued)

*Primary Examiner* — Jason Flick
*Assistant Examiner* — Anh Bui
(74) *Attorney, Agent, or Firm* — Kriegsman & Kriegsman

(57) ABSTRACT

The injection device includes a static structure including a first gear member. The injection device also includes a dynamic structure including a medicine container, a mechanism for pushing liquid medicine out of the medicine container for its injection to a patient, and a second gear member engaged with the first gear member. The injection device additionally includes a drive member for driving one of the first and second gear members so as to cause the dynamic structure to move relative to the static structure along a predetermined direction due to the engagement between the first and second gear members. The injection device further includes a clutch mechanism for maintaining engagement between the first and second gear members in normal condition of the injection device, and for allowing disengagement of the first and second gear members upon a shock received by the injection device along the predetermined direction.

9 Claims, 1 Drawing Sheet

(52) U.S. Cl.
CPC .  *A61M 2005/206* (2013.01); *A61M 2005/208* (2013.01); *A61M 2005/2026* (2013.01); *A61M 2005/2073* (2013.01); *A61M 2005/2418* (2013.01)

(56) References Cited

FOREIGN PATENT DOCUMENTS

| WO | 2005077441 A2 | 8/2005 |
| WO | 2007088444 A1 | 8/2007 |
| WO | 2013186618 A1 | 12/2013 |
| WO | 2013186619 A1 | 12/2013 |

\* cited by examiner

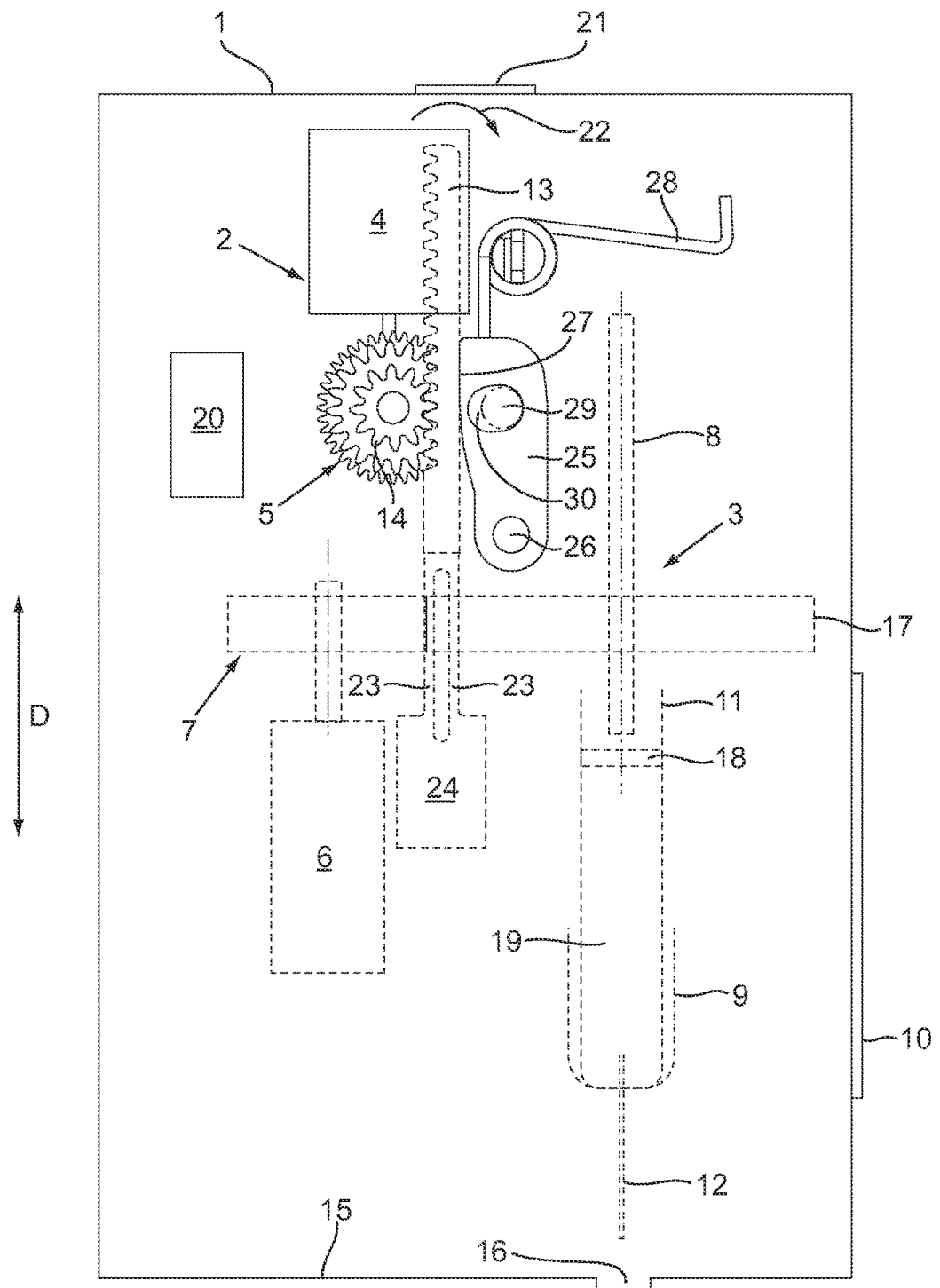

INJECTION DEVICE

The present invention relates to an injection device for injecting liquid medicine to a patient, of the type comprising a medicine container, such as a cartridge, connectable to a needle.

In WO 2005/077441 is described a device comprising, inside a housing, a cartridge holder for receiving and holding a cartridge, first electromechanical means for axially moving a piston of the cartridge to deliver medicine to a patient, and second electromechanical means for axially moving a structure including the cartridge holder and the first electromechanical means to retract the cartridge with the needle connected to it in the housing when not used and to move the cartridge with the needle towards the outside of the housing for piercing the patient's skin and injecting a medicine dose.

A problem with such a device is that the interface between the said structure and the second electromechanical means is sensitive to shocks received by the device, especially in the axial direction. Thus, if the device is dropped a risk exists that the connection between the said structure and the second electromechanical means will break.

The present invention aims at remedying this problem, at least partly. To this end, there is provided an injection device for injecting liquid medicine to a patient, comprising:
  a static structure comprising a first gear member,
  a dynamic structure comprising a medicine container, means for pushing liquid medicine out of said medicine container for its injection to a patient, and a second gear member engaged with the first gear member,
  a drive member for driving one of the first and second gear members so as to cause the dynamic structure to move relative to the static structure along a predetermined direction due to the engagement between the first and second gear members, and
  clutch means for maintaining engagement between the first and second gear members in normal condition of the injection device, and for allowing disengagement of the first and second gear members upon a shock received by the injection device along the predetermined direction.

Typically, said one of the first and second gear members is a wheel and the other of the first and second gear members is a rack.

In a preferred embodiment, the drive member is mounted on the static structure and said one of the first and second gear members is the first gear member.

Preferably, the clutch means comprise:
  means for allowing the other of the first and second gear members to move away from said one of the first and second gear members and thus disengage from said one of the first and second gear members,
  a blocking member which, in a predetermined position, prevents the other of the first and second gear members from moving away from said one of the first and second gear members, and
  a return spring for maintaining the blocking member in the predetermined position, the force of said return spring being overcomeable by the other of the first and second gear members upon a shock received by the injection device along the predetermined direction and moving the other of the first and second gear members away from said one of the first and second gear members.

The means for allowing the other of the first and second gear members to move away from said one of the first and second gear members may comprise at least one flexible member through which the other of the first and second gear members is mounted in the injection device.

Advantageously, the predetermined position of the blocking member is a rest position in which the blocking member is maintained by the return spring against a stop member.

The stop member may be a pin engaged in an oblong opening of the blocking member.

The blocking member may be a lever.

The drive member may be an engine.

The means for pushing liquid medicine out of the medicine container may comprise a piston rod, a transmission for driving the piston rod and a second drive member for driving the transmission. The second drive member may be an engine.

Other features and advantages of the present invention will be apparent upon reading the following detailed description made with reference to the annexed diagrammatic FIGURE which shows an injection device according to a preferred embodiment of the invention.

In the following the term "wheel" will indistinctively designate a wheel or a pinion.

With reference to the annexed FIGURE, an injection device according to the present invention comprises, inside a housing 1, a static structure 2, i.e. a structure which as a whole is fixed relative to the housing 1, and a dynamic structure 3, i.e. a structure which as a whole is moveable relative to the housing 1. The static structure 2 is shown in continuous lines. The dynamic structure 3 is shown in broken lines. The static structure 2 comprises a body (not shown) and, mounted on the body, an engine 4 and a transmission or gearbox 5 driven by the engine 4. The dynamic structure 3 comprises a body (not shown) and, mounted on this body, an engine 6, a transmission 7 driven by the engine 6, a piston rod 8 and a cartridge holder 9. The dynamic structure 3 is moveable in the longitudinal direction D of the device inside the body of the static part 2. The housing 1 has a door 10 for enabling insertion or removal of a medicine cartridge 11 into/from the device, for example in the manner as described in WO 2005/077441. When inserted in the device, the medicine cartridge 11 is supported by the cartridge holder 9. A needle 12 is connectable to the cartridge 11 at an end thereof. The piston rod 8 and, when inserted in the device, the cartridge 11 and the needle 12 all extend in the longitudinal direction D.

For its displacement relative to the housing 1 and the static structure 2, the dynamic structure 3 comprises a rack 13 extending along the longitudinal direction D and which meshes with a gear wheel 14 of the transmission 5. Thus, actuating the engine 4 moves the rack 13 and, with it, the dynamic structure 3 towards or away from a skin contact wall 15 of the housing 1 depending on the rotation direction of the shaft of the engine 4. The dynamic structure 3 may be moved between a retracted position in which the needle 12 is fully inside the housing 1 (as shown in the drawing), thus protecting the user from risks of injury, and an operating position in which the needle 12 protrudes outside the housing 1 through an opening 16 provided in the skin contact wall 15 to pierce the patient's skin.

The piston rod 8 may be displaced along the longitudinal direction D relative to the body of the dynamic structure 3 by actuating the engine 6. To this effect, in a manner known per se, one 17 of the gear wheels of the transmission 7 has an internal thread (not shown) that cooperates with a thread provided on the surface of the piston rod 8, and an annular locking member (not shown) fixed on the body of the dynamic structure 3 has internal projections that cooperate with longitudinal grooves of the piston rod 8 to prevent the piston rod 8 from rotating. Thus, actuating the engine 6 moves the piston rod 8 towards or away from the skin contact wall 15 depending on the rotation direction of the shaft of the engine 6. When moved towards the skin contact wall 15, the piston rod 8 pushes a piston 18 in the cartridge 11 which in turn pushes liquid medicine 19 out of the cartridge 11 through the needle 12 to perform the injection.

A control unit 20 provided in the device may control the engines 4, 6 so as to perform a sequence comprising a first step in which the dynamic structure 3 is moved from its retracted position to its operating position, a second step in which the piston rod 8 is moved to perform the injection and a third step in which the dynamic structure 3 is moved back to its retracted position after the injection of a determined dose has been performed. The said sequence is triggered by the control unit 20 only after a sensor (which may be of the type as described in WO 2007/088444) has detected that the device is placed on the patient's skin and after an injection button 21 has been pressed by the patient. The moveability of the dynamic structure 3 may also be used to connect the needle 12 to the cartridge 11, before use of the device, in the manner as described in WO 2005/077441.

In accordance with the present invention, clutch means are provided to protect the interface between the static and dynamic structures 2, 3, namely the device portion including the rack 13 and the gear wheel 14, from shocks received by the device. Indeed, in the case of shocks subjecting the device to forces oriented along the longitudinal direction D, typically in the case the device is dropped, the rack 13 and/or gear wheel 14 could break due to the engagement of the teeth of the rack 13 with the teeth of the gear wheel 14 and due to the weight of the dynamic structure 3. To avoid this, the rack 13 is elastically mounted on the body of the dynamic structure 3 and may thus incline with respect to the longitudinal direction D, as shown by arrow 22. More precisely, the rack 13 is connected via flexible arms 23 to a plate 24 fixed to the body of the dynamic structure 3. The rack 13, the arms 23 and the plate 24 may be parts of a single piece. The arms 23 may bend transversely to the longitudinal direction D and cause the rack 13 to incline. In normal condition or use of the device, the rack 13 is maintained parallel to the longitudinal direction D by a lever 25. The lever 25 is mounted on the static structure 2, about a pivot 26, and has a contact surface 27 against which the rear surface of the rack 13, i.e. the surface opposite the rack toothed surface, may rest. The lever 25 is subjected to the action of a return spring 28 mounted on the static structure 2. The spring 28 maintains the lever 25 against a stop pin 29 fixed on the static structure 2 and engaged in an oblong opening 30 of the lever 25. In this rest position, the lever 25 prevents the rack 13 from disengaging from the gear wheel 14 without pressing the rack 13 against the gear wheel 14, thanks to the stop pin 29, thus avoiding friction losses during normal displacements of the rack 13. When a shock is received by the device along the longitudinal direction D, the teeth of the rack 13 engaged with the teeth of the gear wheel 14 slide on the teeth of the gear wheel 14, causing the rack 13 to move away from the gear wheel 14 in the direction of arrow 22 due to the shape of the teeth (which may be conventional). During this motion of the rack 13, the lever 25 is pushed by the rack 13 and caused to rotate against the force of the spring 28 within the range of motion permitted by the pin 29 and the oblong opening 30. The rack 13 is thus disengaged from the gear wheel 14 so that the dynamic structure 3 is free to move along the longitudinal direction D under the force generated by the shock. Once the shock is over, the spring 28 returns the lever 25 and the rack 13 into their normal position where the rack 13 is engaged with the gear wheel 14. One will note that the stop pin 29 limits the motion of the lever 25 and thus protects the rack 13 and the flexible arms 23 during the shock. After the shock, a re-initialisation of the device may be performed to move the dynamic structure 3 back to the position where it was before the shock, i.e. generally the retracted position.

Thus, the flexible arms 23, the lever 25 and the return spring 28 define clutch means that maintain engagement between the rack 13 and the gear wheel 14 under normal conditions but allow the rack 13 to disengage from the gear wheel 14 upon a shock received by the device in the longitudinal direction D. Thanks to the present invention, the most shock sensitive portion of the device is protected.

The present invention has been described above by way of example only. It will be clearly apparent to a skilled person that modifications may be made without departing from the scope of the appended claims. For example, the rack 13 could be mounted on the static structure 2 and the engine 4, the transmission 5, the lever 25 and the return spring 28 could be mounted on the dynamic structure 3. According to another modification, the rack 13 could be mounted in the device so as to be moveable in translation transversely to the direction D, instead of being elastically mounted though the flexible arms 23.

The invention claimed is:

1. Injection device for injecting liquid medicine to a patient, comprising:
   a static structure comprising a first gear member,
   a dynamic structure comprising a medicine container, means for pushing liquid medicine out of said medicine container for its injection to a patient, and a second gear member engaged with the first gear member,
   a drive member for driving one of the first and second gear members so as to cause the dynamic structure to move relative to the static structure along a predetermined direction due to the engagement between the first and second gear members, and
   clutch means for maintaining engagement between the first and second gear members in normal condition of the injection device, and for allowing disengagement of the first and second gear members upon a shock received by the injection device along the predetermined direction,
   said clutch means comprising:
   means for allowing the other of the first and second gear members to move away from said one of the first and second gear members and thus disengage from said one of the first and second gear members, wherein the means for allowing the other of the first and second gear members to move away from said one of the first and second gear members comprise at least one flexible member through which the other of the first and second gear members is mounted in the injection device,
   a blocking member which, in a predetermined position, prevents the other of the first and second gear members from moving away from said one of the first and second gear members, and
   a return spring for maintaining the blocking member in the predetermined position, the force of said return spring being overcomeable by the other of the first and second gear members upon a shock received by the injection device along the predetermined direction and moving the other of the first and second gear members away from said one of the first and second gear members.

2. Injection device according to claim 1, wherein said one of the first and second gear members is a wheel and the other of the first and second gear members is a rack.

3. Injection device according to claim 1, wherein the drive member is mounted on the static structure and said one of the first and second gear members is the first gear member.

4. Injection device according to claim 1, wherein the predetermined position of the blocking member is a rest position in which the blocking member is maintained by the return spring against a stop member.

5. Injection device according to claim 4, wherein the stop member is a pin engaged in an oblong opening of the blocking member.

6. Injection device according to claim 1, wherein the blocking member is a lever.

7. Injection device according to claim 1, wherein the drive member is an engine.

8. Injection device according to claim 1, wherein the means for pushing liquid medicine out of the medicine container comprise a piston rod, a transmission for driving the piston rod and a second drive member for driving the transmission.

9. Injection device according to claim 8, wherein the second drive member is an engine.

* * * * *